United States Patent [19]

Oppenläender et al.

[11] 4,115,314
[45] Sep. 19, 1978

[54] PRODUCTION OF WATER-IN-OIL EMULSIONS

[75] Inventors: Knut Oppenläender, Ludwigshafen; Karl Seib, Weinheim; Heinz Krapf, Hessheim, all of Fed. Rep. of Germany

[73] Assignee: BASF Aktiengesellschaft, Rheinland, Pflaz, Fed. Rep. of Germany

[21] Appl. No.: 755,582

[22] Filed: Dec. 29, 1976

Related U.S. Application Data

[62] Division of Ser. No. 630,635, Nov. 10, 1975, abandoned.

[30] Foreign Application Priority Data

Nov. 22, 1974 [DE] Fed. Rep. of Germany ....... 2455287
Aug. 16, 1975 [DE] Fed. Rep. of Germany ....... 2536597

[51] Int. Cl.$^2$ .............................................. B01J 13/00
[52] U.S. Cl. ..................... 252/309; 252/312; 252/314; 252/351; 252/522; 252/DIG. 1; 424/170; 424/172
[58] Field of Search ......... 252/309, 314, 351, DIG. 1; 424/170, 172

[56] References Cited

U.S. PATENT DOCUMENTS

| 3,206,410 | 9/1965 | Moller et al. .................. 252/309 |
| 3,427,248 | 2/1969 | Lamberti et al. ............ 260/615 R X |
| 3,671,458 | 6/1972 | Sherman et al. ............. 260/615 B X |
| 3,748,276 | 7/1973 | Schmolka ...................... 252/316 |
| 3,829,506 | 8/1974 | Schmolka et al. ............... 252/307 X |
| 3,926,840 | 12/1975 | Wendler et al. ................ 252/309 X |

FOREIGN PATENT DOCUMENTS 887,442  1/1962  United Kingdom ..................... 252/351

OTHER PUBLICATIONS

Griffin: "Calculation of HLB Values of Non-Ionic Surfactants", The American Perfumer & Essential Oil Review; May, 1955, pp. 26–29.

*Primary Examiner*—Richard D. Lovering
*Attorney, Agent, or Firm*—Keil, Thompson & Shurtleff

[57] ABSTRACT

A process for the manufacture of reaction products of fatty alcohols and epichlorohydrin, which have been reacted with polyhydric alcohols or their monoethers and may or may not have been further modified with alkylene oxides, the reaction products per se and emulsifiers, solubilizing agents and fat-like materials consisting of these products.

3 Claims, No Drawings

PRODUCTION OF WATER-IN-OIL EMULSIONS

This is a division of application Ser. No. 630,635, filed Nov. 10, 1975 and now abandoned.

The present invention relates to a novel process for the manufacture of reaction products of fatty alcohols, epichlorohydrin and polyhydric alcohols, which products may or may not be modified with alkylene oxides. The resulting mixtures of compounds are — depending on the degree of oxyalkylation and/or the nature of the alkylene oxide-valuable water-in-oil emulsifiers, oil-in-water emulsifiers, solubilizing agents or fat-like materials which are all in the main used in the field of cosmetics.

Water-in-oil emulsifiers are required for incorporating an aqueous phase into an oil or fat so that the latter acquires a readily spreadable consistency (ointments, creams, lotions or make-up). They are also needed for the administration of active ingredients in pharmacy. Industrially, they are used in emulsion polymerization and in water-in-oil dispersions of polymers. Examples of water-in-oil emulsifiers hitherto used are wool grease (lanolin) and lanolin alcohol derivatives, fatty acid esters of hexitols, eg. sorbitan sesquioleate, as well as fatty acid monoglycerides, pentaerythritol fatty acid esters, fatty alcohol citrates and fatty alcohol oxyalkylates. German Printed Application No. 2,023,786 discloses, eg., glycerol esters of wool wax acids for these purposes.

Whilst these water-in-oil emulsifiers are suitable for special applications, they frequently suffer from disadvantages. Often, they are not stable to acids or alkalis. For example, lanolin esters and fatty acid esters are not resistant to saponification, which, eg. limits their use in the cosmetics industry since it is known that after saponification the unpleasant odor of the free fatty acids is perceptible. Furthermore, the stability of the emulsions is frequently no more than moderate, and the emulsions are not universally applicable to all materials in conjunction with which they may have to be used.

Oil-in-water emulsifiers are required for incorporating an oil phase into water so as to produce a stable aqueous emulsion. These emulsifiers must again be stable on storage, and resistant to chemicals, and are used, in the cosmetics field, above all to produce fluid emulsions (lotions).

Solubilizing agents are materials which enable two mutually insoluble materials to be mixed with one another so as to produce a clear, stable solution. They are used, above all, to solubilize essential oils (for perfume formulations).

Fat-like materials are materials which in physical behavior resemble fats, but which must be chemically resistant and stable to heat.

It is an object of the present invention to provide materials which, in accordance with their special structure, display the above effects, and which are chemically stable.

It is a further object of the present invention to provide a method for making emulsifiers, solubilizing agents and fat-like materials which can be employed in cosmetics.

We have found that this object is achieved by a process for the manufacture of novel reaction products, which have the acid properties, wherein saturated or unsaturated fatty alcohols of 10 to 22 carbon atoms, preferably of 16 to 20 carbon atoms, or their mixtures, are reacted with epichlorohydrin in the molar ratio of from 1:0.5 to 1:1.5, preferably about 1:1, and the resulting glycidyl ethers are reacted with polyhydric alcohols of 2 to 6 carbon atoms containing from 2 to 6 hydroxyl groups, or their monoethers with fatty alcohols of 10 to 22 carbon atoms, in the molar ratio glycidyl ether:-polyhydric alcohol or ether = from 1:0.5 to 1:6.0, in the presence of acids or bases.

A modified method is to manufacture the glycidyl ethers and the further reaction products in a one-step reaction, wherein fatty alcohols and epichlorohydrin, in the stated molar ratios, and the polyhydric alcohols, also in the stated molar ratios, which in this case are based on epichlorohydrin, are reacted conjointly in the presence of the acid catalysts and subsequently in the presence of the basic catalysts. In this case, the glycidyl ethers of the polyhydric alcohols may form in addition to the glycidyl ethers of the fatty alcohols, but are, in turn, capable of undergoing addition reaction with the fatty alcohols.

In a further variant, the fatty alcohol glycidyl ether is first manufactured but is not isolated; instead, the polyhydric alcohol (polyol) or a mixture of polyols is added to the reaction mixture and the addition reaction of the glycidyl ether with the polyhydric alcohol or alcohols is then carried out in the same reaction vessel.

Both variants can also be carried out by following the acid-catalyzed addition reaction of the epichlorohydrin by elimination of hydrogen chloride from the chlorohydrin by means of solid powdered alkali metal hydroxide. In each case, water-in-oil emulsifiers are thus produced.

Starting materials for the process according to the invention are fatty alcohols and synthetic long-chain alcohols of 10 to 22 carbon atoms, eg. oleyl alcohol, stearyl alcohol, cetyl alcohol, linolenyl alcohol, myristyl alcohol, lauryl alcohol and tallow fat alcohol and industrially manufactured alcohol mixtures, eg. ALFOLS of 20 to 22 carbon atoms, ALFOLS of 16 to 18 carbon atoms, oxo-alcohols of 17 to 19 carbon atoms and oxo-alcohols of 9 to 11 carbon atoms. Of course, mixtures of the alcohols, including, above all, mixtures of the above naturally occurring alcohols, may also be used.

The alcohols are reacted, in a first step, with epichlorohydrin, using a molar ratio of alcohol to epichlorohydrin of 1:0.5 to 1:1.5, preferably 1:1.

Examples of polyhydric alcohols which, according to the invention, are of 2 to 6 carbon atoms and contain from 2 to 6 hydroxyl groups, or the monoethers derived from such fatty alcohols are: diethylene glycol, dipropylene glycol, 1,4-butanediol, 1,2,4-butanetriol, glycerol, trimethylolpropane, sorbitol, sorbitan, neopentyl glycol, pentaerythritol and, as ethers, the monoethers of the said alcohols, preferably of glycerol, with stearyl alcohol, oleyl alcohol and other alcohols of the above definition, eg. 1-oleyloxy-2,3-propanediol. The fatty alcohol ethers of glycerol may, eg., be produced during the reaction by opening of the epoxide ring of the fatty alcohol glycidyl ether but may also be produced by conventional methods from the fatty alcohol and glycidol or by hydrolysis of the fatty alcohol glycidyl ether, and may react as such, or as mixtures with the above polyhydric alcohols, with the fatty alcohol glycidyl ethers.

Acid or alkaline catalysts may be used for the reactions of the glycidyl ethers with the polyhydric alcohols. Amongst the acid catalysts there may above all be mentioned Lewis acids, eg. boron fluoride etherate, boron fluoride/phosphoric acid, boron fluoride/acetic acid, boron fluoride hydrate, boron fluoride alkylglycol ethereate, tin tetrachloride, zinc chloride, titanium tetrachloride or aluminum chloride, and inorganic acids, eg. sulfuric acid. Suitable alkaline catalysts are alkali metal hydroxides, alkali metal alcoholates or alkaline earth metal alcoholates.

Of course, more than one glycidyl ether may also be reacted, as a mixture or successively, with the polyhydric alcohol or a mixture of polyhydric alcohols.

The reaction is suitably carried out by adding the acid catalyst to the polyhydric alcohol under an inert gas atmosphere at from 5 to 50° C preferably from 20 to 30° C, and then adding the corresponding molar amount of glycidyl ether in the course of from 5 to 60 minutes whilst maintaining the reaction temperature at from 50° to 80° C. The reaction mixture is in general left at the selected temperature for from 1 to 10 hours, preferably from 2 to 8 hours, whilst undergoing mechanical agitation. The catalyst is then neutralized, and the emulsifier is thus obtained directly. If alkaline catalysts are chosen, the reaction temperatures used are in general from 150° to 220° C, but in other respects an analogous method is employed. The emulsifiers manufactured according to the invention are outstandingly suitable for the manufacture of water-in-oil emulsions for cosmetics purposes. Cosmetic preparations, eg. skin creams, in general contain fairly long-chain paraffins, eg. vaseline, at times a waxy component, eg. ozokerite, and also olive oil, as well as glycerides of fatty acids, ie. fats, preservatives, perfume oils and water. The entire system is kept in the desired phase by means of the emulsifiers.

The emulsifiers manufactured according to the invention can be characterized by such data as the density, viscosity, color number and refractive index.

They are, in general, fluid materials which have melting points of from 15° to 60° C, depending on the starting material, densities of from 0.910 to 0.950, viscosities of from 150 to 300 mPa/sec. at 50° C, color numbers of from 2 to 11 and refractive indices of from 1.4000 to 1.5000, measured at 50° C.

Further, we have found that in addition to water-in-oil emulsifiers, oil-in-water emulsifiers, solubilizing agents or fat-like materials may be obtained by carrying out the above reaction and then treating the reaction products with from 1 to 60 moles of one or more alkylene oxides of 2 to 4 carbon atoms.

It is known that the character of a surface-active compound changes with the ratio of the lipophilic component to the hydrophilic component in the molecule, ie. it is possible to convert, for example, a water-in-oil emulsifier into an oil-in-water emulsifier, a solubilizing agent or an oil-soluble fat-like material depending on whether more or less hydrophilic or lipophilic components are incorporated into the molecule.

According to the invention, the above reaction products may be converted, as desired, into materials having the said properties by suitably selecting the degree of oxyalkylation and the alkylene oxides used.

According to the invention, the reaction products obtained by the above methods are in general reacted with from 1 to 60 moles of one or more alkylene oxides of 2 to 4 carbon atoms, depending on the desired properties of the material to be produced. In the text which follows, the abbreviations W/O emulsifier and O/W emulsifier will be used respectively for water-in-oil and oil-in-water emulsifiers.

We have found that on reaction with ethylene oxide alone, modified W/O emulsifiers are obtained at low degrees of oxyethylation, but these can be converted, with increasing degrees of oxyethylation, into O/W emulsifiers and ultimately into solubilizing agents.

If higher alkylene oxides, preferably - according to the invention - 1,2-propylene oxide, 1,2-butylene oxide or mixtures thereof, are used, the products ultimately obtained are oil-soluble synthetic fat-like materials which can be employed in certain formulations, in place of fats of natural origin.

In detail, it is advisable to carry out the process according to the invention as follows:

If the reaction products described above are reacted with from 1 to 5 moles, preferably from 1 to 3 moles, of ethylene oxide, modified W/O emulsifiers are obtained, which have the same emulsifying power as the non-oxyethylated W/O emulsifiers but give softer and smoother W/O emulsions, eg. smoother creams, and are particularly suitable for creams containing hydrocarbons. In respect of heat stability and chemical stability the products are in no way inferior to the non-oxyethylated W/O emulsifiers.

If the ethylene oxide content is increased to from 6 to 20, particularly from 6 to 12, moles of ethylene oxide per mole of W/O emulsifier, O/W emulsifiers which also have good stability characteristics are obtained. These are above all suitable for the manufacture of fluid cosmetic emulsions (lotions).

Finally, if the proportion of ethylene oxide is increased to from 21 to 60 moles, solubilizing agents are obtained, which can above all be employed for solubilizing essential oils (eg. perfume oils).

On reacting the W/O emulsifiers with 1,2-propylene oxide, butylene oxides or both, and especially when using from 1 to 15, preferably from 3 to 10, moles of emulsifier, valuable oil-soluble fat-like materials are obtained, which because of their chemical structure are non-saponifiable, in contrast to natural fats, and are also substantially more stable to heat.

As stated, the oxyalkylation is preferably carried out with ethylene oxide by itself, or with propylene oxide and/or butylene oxide.

Where a reaction with both propylene oxide and butylene oxide is carried out, a mixture of the gases may be introduced, or the alkylene oxides may be used for block-wise adduct formation; in the latter case, the sequence of the blocks is not critical and there are also no limitations on the molar ratio of propylene oxide to butylene oxide.

The oxyalkylation is carried out by conventional methods, with alkaline or acid catalysts, at from 80° to 150° C, in the case of ethylene oxide preferably at from 100° to 120° C and in the case of propylene oxide and/or butylene oxide at from 110° to 140° C, at pressures of from 3 to 10 bars, in closed systems under an inert gas, eg. nitrogen.

Acid catalysts which may be used are, above all, Lewis acids such as $BF_3$, $BF_3$-ethereate, $BF_3$-phosphoric acid, $BF_3$-acetic acid, $BF_3$-dihydrate, $BF_3$-ethylglycol etherate, $SnCl_4$, $ZnCl_2$ or $TiCl_4$, but mineral acids, eg. $H_2SO_4$, HCl or $H_3PO_4$, and their acid salts, may also be used.

Suitable alkaline catalysts are, above all, alkali metal hydroxides, eg. LiOH, NaOH and KOH, alkaline earth metal hydroxides such as $Mg(OH)_2$, $Ca(OH)_2$, $Sr(OH)_2$ and $Ba(OH)_2$, the corresponding oxides or carbonates, alcoholates of 1 to 4 carbon atoms per alcohol radical, above all sodium methylate, sodium ethylate or potassium t.-butylate, and tertiary amines such as trimethylamine, triethylamine or triisopropylamine and, finally, the corresponding quaternary ammonium hydroxides, eg. tetramethylammonium hydroxide.

The Examples of the preparation and the use of the products, which now follow, illustrate the invention; in these, parts are by weight, unless expressly stated otherwise, and parts by volume bear the same relation to parts by weight as that of the milliliter to the gram.

EXAMPLE 1

10.4 parts by volume of boron fluoride diethyl-etherate (47% strength) are added to 96.4 parts (1.05 moles) of glycerol in a round-bottomed flask, whilst stirring under nitrogen at 25° C. 340 parts (1.05 moles) of oleyl glycidyl ether are then added dropwise in the course of 40 minutes whilst keeping the reaction temperature at from 60 to 65° C. The reaction mixture is stirred for 4 hours at 65° C, and the acid catalyst is then neutralized, or removed by means of a basic ion exchanger. A pale yellow clear liquid having very good water-in-oil emulsifying properties is obtained.

EXAMPLE 2

0.3 part by volume of boron fluoride etherate is added to 60.4 parts (0.57 mole) of 1,2,4-butanetriol under nitrogen at 25° C. 200 parts (0.57 mole) of oleyl glycidyl ether are added to this mixture in the course of 50 minutes whilst keeping the reaction temperature at from 60° to 65° C. The batch is then stirred for 4 hours at 65° C, after which the temperature is raised to 100° C and kept thereat for 3 hours. Small amounts of unconverted butanetriol are removed and a clear pale yellow liquid having very good emulsifying properties is obtained.

EXAMPLE 3

115 parts (1.25 moles) of glycerol, 400 parts (1.25 moles) of the glycidyl ether of an oxo alcohol of 17 to 19 carbon atoms, and 3.5 parts of sodium methylate are heated to 190°-200° C under nitrogen, whilst stirring vigorously, and kept at this temperature for 5 hours. After removing a small amount of unreacted glycerol, a colorless solid having good water-in-oil emulsifying properties is obtained.

EXAMPLE 4

0.8 part of sodium methylate is added to 26.8 parts (0.2 mole) of trimethylolpropane and 129.6 parts (0.4 mole) of oleyl glycidyl ether under nitrogen and the mixture is heated at 200° C for 5 hours, with vigorous stirring. After completion of the reaction, a pale yellow clear liquid having very good water-in-oil emulsifying properties is obtained.

EXAMPLE 5

28 parts (0.3 mole) of glycerol, 97.2 parts (0.3 mole) of oleyl glycidyl ether and 0.7 part by volume of 45% strength $BF_3$-phosphoric acid are heated at 100° C for 5 hours under nitrogen, with vigorous stirring. The mixture is allowed to cool and the acid catalyst is removed by treatment with a basic ion exchanger. A clear pale yellow liquid with very good water-in-oil emulsifying properties is obtained.

EXAMPLE 6

0.75 part by volume of boron fluoride etherate is added to 26 parts (0.28 mole) of glycerol under nitrogen. 80 parts (0.28 mole) of lauryl glycidyl ether are then added dropwise in the course of 40 minutes at 60°-65° C, whilst stirring. After removing unreacted glycerol, a pale brown liquid having good water-in-oil emulsifying properties is obtained.

EXAMPLE 7

2 parts by volume of 37% strength boron fluoride/acetic acid are added to 225 parts (2.5 moles) of 1,4-butanediol at 25° C, under nitrogen. 1,000 parts (3.09 moles) of oleyl glycidyl ether are then added dropwise, whilst stirring, in the course of 45 minutes, during which the temperature of the reaction mixture rises to 55° C. The temperature is then raised to 65° C and maintained thereat for 4 hours. After completion of the reaction, a medium-brown liquid having very good water-in-oil emulsifying properties is isolated.

EXAMPLE 8

100 parts by volume of boron fluoride/phosphoric acid are added to 300 parts (3.3 moles) of glycerol at 25° C under nitrogen. 1,000 parts (3.7 moles) of myristyl glycidyl ether are then added whilst stirring and the reaction mixture is heated at 160° C for 5 hours. After cooling, a colorless solid having very good water-in-oil emulsifying properties is isolated.

EXAMPLE 9

1 part by volume of boron fluoride etherate is added to 60.2 parts (0.18 mole) of 1-oleyloxymethylene-1,2-ethanediol at 25° C, under nitrogen. 50.2 parts (0.20 mole) of lauryl glycidyl ether are added dropwise, whilst stirring, in the course of 30 minutes, during which the temperature of the reaction mixture rises to 50° C. After all has been added, the mixture is heated to 65°-70° C and kept thereat for 4 hours. The reaction product, a pale yellow clear liquid, has very good water-in-oil emulsifying properties.

EXAMPLE 10

1.3 parts by volume of boron trifluoride ethyl-etherate are added to 92 parts (1.0 mole) of glycerol and 268.5 parts (1.0 mole) of oleyl alcohol at 25° C under nitrogen. The reaction mixture is heated to 70°-75° C whilst stirring and 92.5 parts (1.0 mole) of epichlorohydrin are added dropwise in the course of 25 minutes. The temperature is then raised to 80° C and the reaction is allowed to proceed at this temperature for 4.5 hours. The mixture is then cooled to 25° C, 44 parts (1.1 moles) of solid powdered sodium hydroxide are added whilst stirring vigorously and the batch is stirred for 15 hours at 25° C. Finally, 2.8 parts of sodium methylate are added and the mixture is heated to 170°-175° C under a descending condenser and kept thereat for 5 hours. After filtering the reaction mixture, a pale yellow clear liquid having very good water-in-oil emulsifying properties is obtained.

The material prepared according to Example 5, eg., has the following characteristics:

| | |
|---|---|
| Physical state: | fluid |
| Density at 50° C: | 0.937 |
| Viscosity at 50° C: | 206 mPas |
| Color number: | from 4 to 7 |
| Refractive index at 50° C: | 1.4620 |

In the preparation of emulsions, it is necessary to carry out work to overcome surface tension. As a rule, one phase, at an elevated temperature (from 70° to 75° C) is run slowly, with vigorous stirring, into the other phase. The temperature of the phase which is added should be 2° C above the phase initially present. In the case of water-in-oil emulsions, the water is best added in small portions to the phase containing the fat and emulsifier. It is necessary to stir the emulsion constantly, but not too vigorously, until it is cold, and then to homogenize it. Important factors are the type of stirring, the duration of stirring, the temperature control and the mechanical system used for homogenization.

The following is an example of the composition of a cream: Vaseline (saturated hydrocarbons of 25 to

| | |
|---|---|
| 50 carbon atoms) | 15.0% by weight |
| Ozokerite (petroleum wax) | 5.0% by weight |
| Olive oil | 10.0% by weight |
| Mixed triglyceride of capric acid and caprylic acid | 10.0% by weight |
| Isopropyl myristate | 5.0% by weight |
| Emulsifier according to the invention, from Example 5 | 5.0% by weight |
| Preservative based on p-hydroxybenzoic acid esters | 0.2% by weight |
| Perfume oil | 0.3% by weight |
| H$_2$O | 49.5% by weight |

The water index is obtained by multiplying the g of water taken up (determined by weighing) by 5.

DETERMINATION OF THE EMULSIFYING POWER

The determination of the emulsifying power with vaseline as the oil phase has proved a reliable quick laboratory method. 35 g of vaseline and 3 g of emulsifier are heated to 70° C in a porcelain dish and the melt is stirred thoroughly. Water at 72° C is added a little at a time, whilst gently stirring by hand using a porcelain pestle. The uptake of 62 g of water is classified as "emulsifying power 100". (Accordingly, "emulsifying power 200" denotes the uptake of 124 g of water.)

If all the parameters are kept constant, the values scatter by 5–10%. The values in the Table are mean values from several measurements.

The Table shows the superiority of the emulsifying power of the new water-in-oil emulsifiers.

STABILITY OF THE EMULSION (CREAM)

Creams (water-in-oil emulsions) were prepared in accordance with the following recipe using the water-

| EMULSIFYING POWER AND EMULSIFYING INDEX (WATER INDEX) | | | |
|---|---|---|---|
| Emulsifiers used | Emulsifying power with vaseline | Emulsifying index with paraffin oil | Stability of the emulsion |
| Emulsifier from Example 1 | 250 | 1,150 | very good |
| Emulsifier from Example 5 | 275 | 1,125 | very good |
| Emulsifier from Example 7 | 245 | 930 | very good |
| Emulsifier from Example 9 | 230 | 850 | very good |
| Wool wax | 145 | 600 | satisfactory |
| Mixed fatty acid/citric acid ester of pentaerythritol | 210 | 645 | satisfactory |
| Glycerol monooleate | 190 | 740 | satisfactory |
| Sorbitan monooleate | 190 | 685 | satisfactory |
| Sorbitan sequioleate | 220 | 800 | good |
| Sorbitan dioleate | 200 | 780 | poor |

DETERMINATION OF THE EMULSIFYING INDEX (WATER INDEX):

(WI = amount of water, in g, taken up by 95 g of paraffin oil and 5 g of emulsifier) The water index gives an indirect picture of the emulsifying capacity of water-in-oil emulsifiers. However, it is important not to read too much into the results, since the emulsification depends on too many other parameters to be predictable from the WI alone. The WI results should be viewed only in relative terms since the method used has a decisive influence on the values obtained.

The determination is carried out as follows:

4 g of emulsifier and 76 g of DAB 7 paraffin oil are thoroughly mixed in a beaker, using a magnetic stirrer (with heating, if appropriate). 20 g of this mixture are introduced, at room temperature, into the mixing bowl of a kitchen mixer (Kenwood Chef) and homogenized for 3 minutes using the whisking attachment. The speed of stirring is set to "100" by means of a regulator. It is then raised to "160" and at half-minute intervals 1 ml of water at room temperature is added. After 20 ml have been taken up, the amounts of water added are increased to 2 ml, and after 50 ml have been taken up they are increased to 5 ml. When the cream slips in the bowl and the water is no longer taken up in the course of about 2 minutes, the optimum water uptake has been reached.

Since the values show a scatter of from about 5 to 10%, the water index determination must be carried out at least 2 or 3 times.

in-oil emulsifiers of the invention. Their stability was tested after extended storage at room temperature (for more than 6 months), after several weeks' test in an oven (at 40° C) or in a refrigerator (at 6° C) and in the rocking test. The Table shows that the stability of the creams prepared using the emulsifiers of the invention is very good. Water-in-oil cream for the stability test:

| | |
|---|---|
| 5.0 | parts by weight of emulsifier |
| 0.2 | part by weight of cetyl alcohol/stearyl alcohol |
| 4.0 | parts by weight of paraffin oil |
| 35.8 | parts by weight of vaseline |
| 55.0 | parts by weight of water |
| 100.0 | |

Heat stability of the emulsifiers:

Commercial water-in-oil emulsifiers and emulsifiers manufactured according to the invention were prepared by keeping them at a low temperature and an elevated temperature (drying oven at 75° C) for 4 weeks. This gave the results shown in the Table which follows:

| | | Oven | |
|---|---|---|---|
| | Refrigerator | without H$_3$PO$_4$ | with H$_3$PO$_4$ |
| Sorbitan sesquioleate | ++ | −− | −− |
| Mixed ester of glycerol and sorbitol | ++ | − | −− |
| Mixed fatty acid/citric acid ester of pentaerythritol | ++ | + | −− |
| Distearyl citrate | | | |

-continued

| | Refrigerator | Oven without H₃PO₄ | Oven with H₃PO₄ |
|---|---|---|---|
| Emulsifier from Example 5 | ++ | ++ | ++ |

++ = odorless = no discoloration
+ = just odorless = at most pale yellow coloration
− = slightly rancid = yellow to brown
− − = unbearably rancid = dark brown The Examples which follow show the preparation and use of the oxyalkylated emulsifiers.

EXAMPLE 11

1,040 parts by weight (2.5 moles) of W/O emulsifier from Example 5 are mixed with 20 parts by volume of $BF_3$-phosphoric acid (45 percent strength) and reacted in a stirred autoclave, at from 80° to 100° C and from 4 to 9 bars pressure, with 110 parts by weight (2.5 moles) of ethylene oxide added a little at a time. After completion of the reaction, the catalyst is neutralized, or removed by treatment with a basic ion exchanger. 1,130 parts by weight of a bright pale brown clear fluid which has excellent water-in-oil emulsifying properties are obtained.

EXAMPLE 12

952 parts by weight (2.3 moles) of water-in-oil emulsifier from Example 7 are mixed, in a stirred autoclave, with 10 parts by weight of sodium hydroxide and reacted with 304 parts by weight (6.9 moles) of ethylene oxide at from 110° to 120° C and from 4 to 9 bars. 1,235 parts by weight of a pale brown fluid which has excellent water-in-oil emulsifying properties are obtained.

EXAMPLE 13

832 parts by weight (2.0 moles) of W/O emulsifier from Example 1 are mixed with 9 parts by weight of potassium hydroxide and the mixture is reacted, in a stirred autoclave, at from 110° to 120° C and from 4 to 9 bars, with 704 parts by weight (16 moles) of ethylene oxide. After completion of the reaction 1,520 parts by weight of a pale brown fluid which has very good oil-in-water emulsifying properties are isolated.

EXAMPLE 14

1,338 parts by weight (3.2 moles) of W/O emulsifier from Example 3 are mixed with 28 parts by volume of boron fluoride/acetic acid and reacted in a stirred autoclave, at from 100° to 110° C and from 4 to 9 bars, with 1,408 parts by weight (32 moles) of ethylene oxide, added a little at a time. 2,710 parts by weight of a pale brown fluid which has very good oil-in-water emulsifying properties are obtained.

EXAMPLE 15

1,165 parts by weight (2.8 moles) of water-in-oil emulsifier from Example 1 are mixed with 13 parts by weight of sodium hydroxide and reacted in a stirred autoclave, at from 110° to 120° C and from 4 to 9 bars, with 3,396 parts by weight (84 moles) of ethylene oxide, added a little at a time. 4,515 parts by weight of a semi-solid pasty pale yellow material which has very good solubilizing properties, are obtained.

EXAMPLE 16

A cream (W/O emulsion) using one of the water-in-oil emulsifiers according to the invention has the following composition:

| | |
|---|---|
| Vaseline | 20.0% by weight |
| Paraffin oil DAB 7 | 5.0% by weight |
| Isopropyl myristate | 1.0% by weight |
| Cetyl alcohol | 0.5% by weight |
| Emulsifier according to the invention, from Example 1 | 1.5% by weight |
| Preservative based on p-hydrobenzoic acid esters | 0.2% by weight |
| Perfume oil | 0.3% by weight |
| Water | 71.5% by weight |

This cosmetic W/O cream is prepared in the same way as that described in Example 10.

EXAMPLE 17

Stable fluid O/W emulsions can be prepared with the oil-in-water emulsifiers manufactured according to the invention. One such lotion has the following composition:

| | |
|---|---|
| Cetyl alcohol | 3.0% by weight |
| Paraffin oil | 3.0% by weight |
| Fatty alcohol oxyethylate | 0.5% by weight |
| Isopropyl myristate | 7.0% by weight |
| Emulsifier according to the invention, from Example 3 | 2.0% by weight |
| Glycerol | 1.0% by weight |
| Preservative based on p-hydroxybenzoic acid esters | 0.1% by weight |
| Perfume oil | 0.2% by weight |
| Water | 83.2% by weight |

This cosmetic lotion is prepared by slowly adding the oil phase, which is at about 70° C and contains the emulsifier, to the water phase, also heated to 70° C, whilst stirring constantly. The emulsion must then be stirred until cold. The lotions prepared using the O/W emulsifiers according to the invention have an attractive milky-white appearance, spread well and produce a pleasant smooth sensation on the skin. They are absorbed rapidly without leaving an objectionable greasy shine. Even after a stability test of several weeks in a refrigerator and in an oven, the lotions exhibited excellent stability.

EXAMPLE 18

Completely clear solutions of ethereal oils, such as mountain pine oil, fir needle oil, lavender oil or perfume compositions in alcoholic or purely aqueous media can be produced with the solubilizing agents manufactured according to the invention. A solubilized product thus prepared, using a solubilizing agent according to the invention, has, eg. the following composition:

| | |
|---|---|
| Perfume oil composition | 1.0% by weight |
| Solubilizing agent according to the invention, from Example 5 | 6.0% by weight |
| Water | 93.0% by weight |

The solubilized product is transparent and clear.

We claim:
1. In a process for the production of water-in-oil emulsions at a temperature of about 70° to 75° C wherein water is added to an oily or fatty phase containing an emulsifier in small portions, said added water having a temperature of about 2° C higher than the temperature of said oily or fatty phase, the improvement which comprises using as the emulsifier a reaction product obtained by the following steps:

(a) reacting saturated or unsaturated fatty alcohols of 16 to 20 carbon atoms, which alcohols are selected from the group consisting of oleyl alcohol, stearyl alcohol, myristyl alcohol, linolenyl alcohol, tallow fat alcohol, ALFOLS of 16 to 18 carbon atoms, oxo alcohols of 17 to 19 carbon atoms and mixtures thereof, with epichlorohydrin in the presence of an acid catalyst, and eliminating hydrogen chloride from the chlorohydrin by means of solid powdered alkali metal hydroxide, the molar ratio of alcohol to epichlorohydrin being from 1:0.5 to 1:1.5; and (b) reacting the glycidyl ethers produced in step (a) with polyhydric alcohols of 2 to 6 carbon atoms and containing from 2 to 6 hydroxyl groups, said polyhydric alcohols being selected from the group consisting of ethylene glycol, dipropylene glycol, 1,4-butanediol, 1,2,4-butanetriol, glycerol, trimethylolpropane sorbitol, neopentyl glycol, and pentaerythritol, or with monoethers of said alcohols with fatty alcohols of 10 to 22 carbon atoms per fatty alcohol radicals, in a molar ratio of glycidyl ether to polyhydric alcohol or ether of from 1:1.5 to 1:6.0, the reaction of the glycidyl ether with the polyhydric alcohol or ether being carried out in the presence of Lewis acids selected from the group consisting of boron fluoride etherate, boron fluoride/phosphoric acid, boron fluoride/acetic acid, boron fluoride hydrate, boron fluoride alkylglycol etherate, tin tetrachloride, zinc chloride, titanium tetrachloride and aluminum chloride and sulfuric acid or in the presence of alkaline catalysts selected from the group consisting of alkali metal hydroxides, alkaline earth metal hydroxides, the corresponding oxides, carbonates, alcoholates of 1 to 4 carbon atoms per alcohol radical, tertiary amines and the corresponding quaternary ammonium hydroxides.

2. The process as set forth in claim 1 wherein the emulsifier has been ethoxylated with from 1 to 5 moles of ethylene oxide.

3. The process as set forth in claim 1 wherein the emulsifier has been prepared with an unsaturated alcohol as starting material.

* * * * *